US010010277B2

(12) United States Patent
Carp et al.

(10) Patent No.: US 10,010,277 B2
(45) Date of Patent: Jul. 3, 2018

(54) CANCER DETECTION BY OPTICAL MEASUREMENT OF COMPRESSION-INDUCED TRANSIENTS

(75) Inventors: Stefan A. Carp, Cambridge, MA (US); David Alan Boas, Winchester, MA (US)

(73) Assignee: The General Hospital Corporation, Boston, MA (US)

( * ) Notice: Subject to any disclaimer, the term of this patent is extended or adjusted under 35 U.S.C. 154(b) by 839 days.

(21) Appl. No.: 11/766,444

(22) Filed: Jun. 21, 2007

(65) Prior Publication Data

US 2008/0004531 A1 Jan. 3, 2008

Related U.S. Application Data

(60) Provisional application No. 60/805,537, filed on Jun. 22, 2008.

(51) Int. Cl.
*A61B 5/1455* (2006.01)
*A61B 5/00* (2006.01)
*A61B 6/00* (2006.01)

(52) U.S. Cl.
CPC ........ *A61B 5/14551* (2013.01); *A61B 5/0053* (2013.01); *A61B 6/507* (2013.01)

(58) Field of Classification Search
CPC ................................. A61B 8/06; A61B 8/483
USPC ....... 600/407, 410, 415, 419, 421, 425, 473, 600/437, 438, 441, 453–456
See application file for complete search history.

(56) References Cited

U.S. PATENT DOCUMENTS

| | | | | |
|---|---|---|---|---|
| 3,638,640 A * | 2/1972 | Shaw | ........................... | 600/323 |
| 4,618,973 A * | 10/1986 | Lasky | ............................. | 378/37 |
| 4,671,295 A * | 6/1987 | Abrams et al. | ............... | 600/463 |
| 5,372,135 A | 12/1994 | Mendelson et al. | | |
| 5,555,885 A * | 9/1996 | Chance | ......................... | 600/431 |
| 5,899,865 A * | 5/1999 | Chance | ......................... | 600/473 |
| 6,128,517 A * | 10/2000 | Maki et al. | .................. | 600/310 |
| 8,298,148 B2 * | 10/2012 | Furman | ......................... | 600/453 |
| 2001/0033364 A1 * | 10/2001 | Cabib et al. | .................. | 351/221 |
| 2003/0009090 A1 * | 1/2003 | Jeon et al. | ..................... | 600/323 |
| 2004/0162468 A1 * | 8/2004 | Cheng | ............... | A61B 5/14546 600/310 |
| 2005/0008117 A1 | 1/2005 | Livingston | | |
| 2005/0197583 A1 * | 9/2005 | Chance | ......................... | 600/476 |
| 2006/0063995 A1 * | 3/2006 | Yodh et al. | .................. | 600/323 |
| 2007/0027371 A1 * | 2/2007 | Benaron et al. | ............. | 600/310 |

OTHER PUBLICATIONS

De Blasi, Robert A. et al.; "Noninvasive measurement of forearm blood flow and oxygen consumption by near-infrared spectroscopy," 1994, Journal of Appl. Physiology, vol. 76(3), pp. 1388-1393.*

(Continued)

*Primary Examiner* — Jennifer Dieterle
*Assistant Examiner* — Vani Gupta
(74) *Attorney, Agent, or Firm* — Quarles & Brady LLP

(57) ABSTRACT

A cancer screening method includes changing a compression state of selected tissue; and obtaining a signal indicative of a response of an optical property of the selected tissue in response to the change in the compression state.

25 Claims, 13 Drawing Sheets

(56) References Cited

OTHER PUBLICATIONS

Fantini, Sergio, "A haemodynamic model for the physiological interpretation of in vivo measurements of the concentration and oxygen saturation of haemoglobin," 2002, Physics in Medicine and Biology, vol. 47, pp. N249-N257.*
Fantini, et al., "Quantitative Determination of the Absorption Spectra of Chromophores in Strongly Scattering Media: A Light-Emitting-Diode Based Technique", *Appl. Opt*; vol. 33, No. 22, (Aug. 1994), pp. 5204-5213.
Fantini, et al., "Semi-Infinite-Geometry Boundary Problem for Light Migration in Highly Scattering Media: A Frequency-Domain Study in the Diffusion Approximation", *J. Opt. Soc. Am. B.*, vol. 11, No. 10, (Oct. 1994), pp. 2128-2138.
Berkow, et al., "Common Medical Tests", *The Merck Manual of Medical Information* (*Home Edition*), Chapter A.III, (1997), pp. 1375-1380.
PCT Notification of Transmittal of the International Search Report and The Written Opinion of the International Searching Authority, or the Declaration (dated Jul. 2008).
Notification Concerning Transmittal of International Preliminary Report on Patentability for International Application No. PCT/US2007/071763 dated Apr. 16, 2009.

\* cited by examiner

CANCER DETECTION BY OPTICAL MEASUREMENT OF COMPRESSION-INDUCED TRANSIENTS

CROSS-RELATED APPLICATION

Under 35 U.S.C. 119(e)(1), this application claims the benefit of provision application Ser. No. 60/805,537, filed Jun. 22, 2006, and entitled, "Cancer Detection by Optical Measurement of Compression-Induced Transients."

STATEMENT REGARDING FEDERALLY SPONSORED RESEARCH

This invention was made with government support under Grant Number CA097305 awarded by the National Institutes of Health. The government has certain rights in the invention.

BACKGROUND

Breast cancer is the most common cancer afflicting females. Although there exist treatments for curing breast cancer, a significant percentage of such treatment fail.

As with most cancers, the likelihood of success in treatment depends in part on how early the cancer is detected. Conventional methods of detecting breast cancer rely on self-examination and/or mammograms for screening, followed in some cases by biopsies. A biopsy is an invasive procedure that can result in patient discomfort. Moreover, it is a time-consuming and resource-intensive procedure. It is therefore not the method of choice for screening large populations.

A known non-invasive method for detecting breast cancer is to perform MRI on the breast. MRI, however, is a resource-intensive procedure that, because of poor specificity, result in more false alarms than mammography. In addition, MRI is not completely non-invasive since it requires injection of a chemical agent.

SUMMARY

In one practice, the invention features a cancer screening method that includes changing a compression state of selected tissue; and obtaining a signal indicative of a response of an optical property of the selected tissue in response to the change in the compression state.

Some practices of the invention include the additional step of determining an oxygen consumption profile at least in part on the basis of the signal. Other practice of the invention include the additional step of determining a profile of volumetric rate of blood flow in the selected tissue at least in part on the basis of the signal.

Other practices also include selecting the selected tissue to be breast tissue.

In addition, there exist practices in which changing the compression state includes applying a constant pressure to the selected tissue. In some practices, the constant pressure is selected to be less than approximately 6 lbs.

In additional practices, obtaining the first measurement includes illuminating the tissue with near-infrared radiation.

In yet other practices, obtaining the first measurement includes detecting near-infrared radiation scattered from within the tissue.

In further practices, determining a profile of volumetric rate of blood flow includes applying a constraint specifying that blood flow into the selected tissue is equal to blood flow out of the selected tissue.

In yet further practices, determining a profile of volumetric rate of blood flow includes applying a rule that allows blood flow into the selected tissue to be different than blood flow out of the selected tissue.

In another aspect, the invention features a cancer screening method that includes causing selected tissue to undergo a transition between a first compression state and a second compression state; obtaining a measurement of a time-dependent optical property of blood within the selected tissue; and at least in part on the basis of the measurement, determining whether the tissue contains a tumor.

In some practices, determining whether the tissue contains a tumor includes comparing the measurement with a model of an expected change in the time-dependent optical property. This can include, for example, estimating a value of a model parameter on the basis of the measurement, selecting the model parameter to be a model parameter indicative of oxygen consumption by the selected tissue, and/or selecting the model parameter to be a model parameter indicative of volumetric blood flow rate within the tissue.

In another aspect, the invention features a cancer-screening apparatus that includes a force applicator for selectively placing selected tissue in one of a plurality of compression states; a source of electromagnetic radiation for illuminating the selected tissue; a detector for detecting electromagnetic radiation scattered from within the selected tissue; and a processor coupled to receive a signal from the detector, the processor being configured to estimate at least one of oxygen consumption and blood flow of the selected tissue based at least in part on a signal provided by the detector.

In another aspect, the invention features a cancer screening method that includes causing selected tissue to undergo a transition between a first compression state and a second compression state; obtaining a measurement of a time-dependent optical property of blood within the selected tissue; and generating tomographic images of the selected tissue based on the time-dependent optical property with the tomographic images showing a physiological parameter associated with subvolumes of the selected tissue and with the physiological parameter being indicative of cancer.

In some practices, the physiological parameter is one of oxygen consumption and blood flow. A first subvolume of the selected tissue is identified as cancerous based on an analysis of the physiological parameter associated with the first subvolume. The physiological parameter is oxygen consumption, and identifying includes determining that the oxygen consumption of the first subvolume is above a predefining value. A three-dimensional image of the selected tissue is constructed from the tomographic images. The source of electromagnetic radiation includes a near-infrared source.

Other embodiments include those in which the processor is configured to determine an oxygen consumption profile at least in part on the basis of the signal, and those in which the processor is configured to determine a profile of volumetric rate of blood flow in the selected tissue at least in part on the basis of the signal, and those in which the processor is configured to determine both of the foregoing quantities at least in part on the basis of the signal.

In some embodiments, the force applicator is configured to apply a constant pressure to the selected tissue. In some of these embodiments, the force applicator is configured to apply a constant pressure of less than approximately 6 lbs.

DETAILED DESCRIPTION

Because of its high metabolic activity, cancerous tissue is characterized by an unusually high appetite for oxygen. Since it is the blood that carries oxygen to tissue, this high appetite for the oxygen is often accompanied by an unusually high blood flow.

The screening method described herein seeks to measure both volumetric blood flow and oxygen consumption in tissue, and in particular, in breast tissue, by illuminating the tissue with electromagnetic radiation. As described herein, the particular electromagnetic radiation is near-infrared radiation, which is selected both because of its interaction with hemoglobin and because breast tissue efficiently transmits such radiation.

The screening method begins with the application of a compression force, or pressure, to compress the breast. In principle, any level of compression will suffice. However, in practice, the level of compression is driven by the noise sensitivity of the measurement instrumentation. Present instrumentation is such that useful data can be obtained with compression that is a fraction of that used in mammography.

Compression of the breast results in changes in the breast tissue, including compression of blood vessels in the breast, which in turn reduces volumetric blood flow in the breast. Since the breast tissue has the same appetite for oxygen whether it is compressed or not, and since less blood is available for supplying oxygen to breast tissue, compression causes a local reduction in the concentration of oxygenated hemoglobin and a local increase in the concentration of deoxygenated hemoglobin. Because cancerous tissue consumes more oxygen, the magnitude of the local reduction in the oxygenated hemoglobin concentration is expected to be higher when cancerous tissue is present than it would be if only normal breast tissue were present.

Figure 1A:
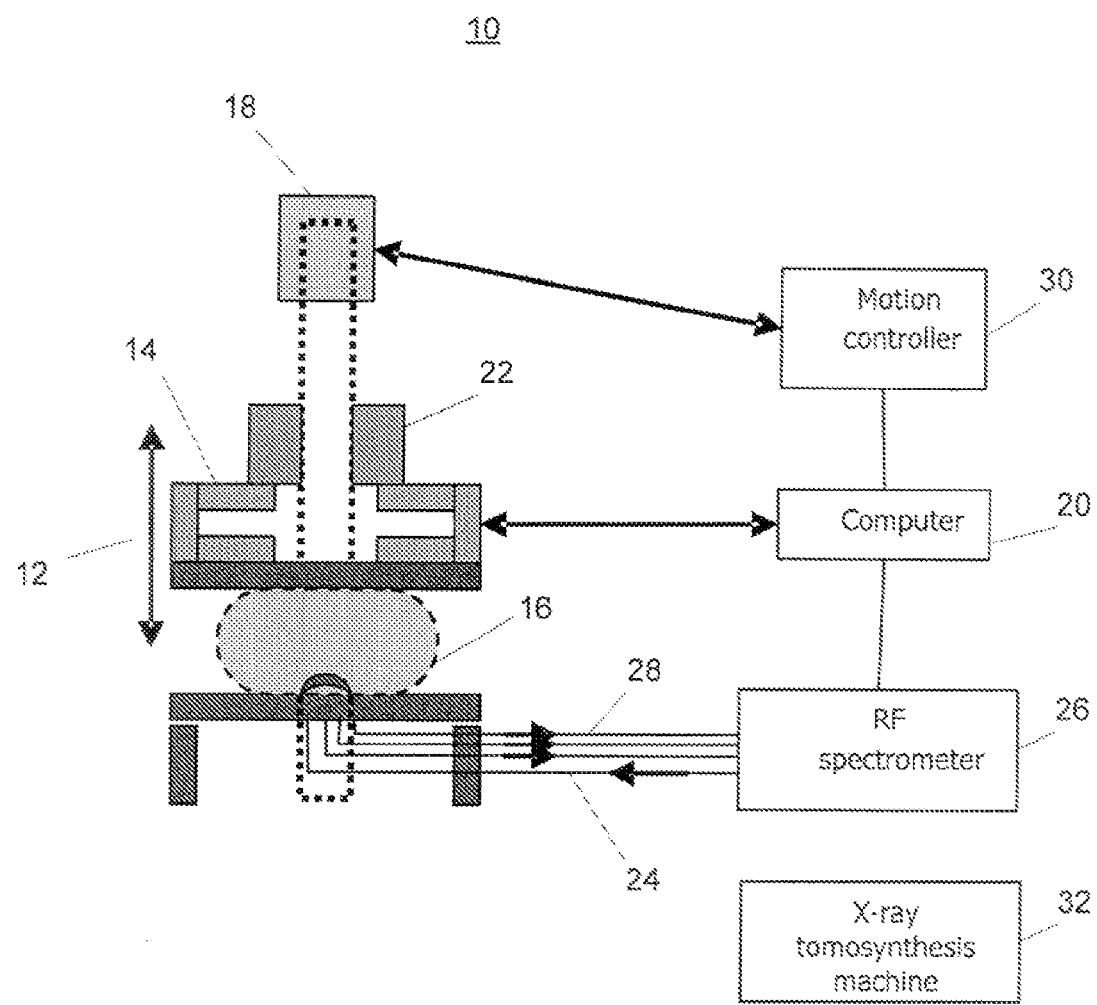
FIG. 1A shows an experimental setup for obtaining optical measurements of compressed breast tissue.

The local concentrations of oxygenated and deoxygenated hemoglobin are measured using known optical methods. Referring to FIG. 1A, a suitable breast compression spectroscopy system 10 includes a computer-controlled translation stage 12 that causes a compression frame 14 to apply a compression force to a breast 16. A stepper motor 18 under the control of a computer 20 causes the compression frame 14 to apply a compression force selected from one of several compression levels. A force transducer 22 integrated into the compression frame 14 provides the computer 20 with a feedback signal indicative of the compression force.

One or more delivery fibers 24 extend from an RF spectrometer 26 to a delivery site on the breast 16. A plurality of collection fibers 28 extend from collection sites on the breast 16 back to the spectrometer 26. The RF spectrometer 26 then provides measurement data to the computer 20 for processing using methods described below.

Measurements can be carried out on a single site on the breast 16, using only a single collection fiber 28 and delivery fiber 24. In such a case, data will only be acquired for a limited volume of breast tissue extending outward from the point at which the collection fiber 28 contacts the breast 16. Measurements can also be made at a plurality of locations which permits the reconstruction of three-dimensional images of the interior of the breast. In the system shown in FIG. 1, collection fibers 28 are connected to various locations on the breast 16. Consequently, the computer 20 can synthesize an image of the breast's interior using known methods of image reconstruction. Measurements from an X-ray tomosynthesis machine 32 may be combined with the optical measurements from the spectrometer 26 to reconstruct three-dimensional images of tissue within the breast 16. An MRI scanner 34 may also be used to acquire measurements.

The screening method includes carrying out such measurements in one or more compression states, each characterized by a different compression plateau. The resulting serial measurements provide insight into the dynamics associated with transient changes in optical properties. Furthermore, by comparing these measurements with a model of this transient state, estimates of volumetric blood flow (BF) and oxygen consumption (OC) can be obtained.

One suitable model for the transient state is that based on a differential equation that relates the amount of oxygenated hemoglobin in an infinitesimal tissue volume to both the oxygen consumption in that volume and to the flow of arterial blood into and venous blood out of that volume. A differential equation that describes a mass balance for oxygenated hemoglobin ($HbO_2$) within a particular measurement volume can be written as follows:

$$\frac{dN_{HbO2}}{dt} = -\frac{OC}{4} + F_{in}[HbT]_{blood}S_{a,O_2} - F_{out}[HbT]_{blood}S_{v,O_2} \quad (1)$$

where $N_{HbO2}$ is the molar amount of oxygenated hemoglobin within the measurement volume;

OC is the oxygen consumption (in moles $O_2$/second) within the measurement volume, quartered to reflect the fact that each saturated hemoglobin molecule carries four oxygen atoms;

$F_{in}$ and $F_{out}$ are the volumetric blood flows into and out of the measurement volume (in liters/second);

$[HbT]_{blood}$ is the total blood hemoglobin concentration (in moles/liter);

$S_{a,O_2}$ is the oxygen saturation of arterial blood entering the measurement volume; and $S_{v,O_2}$ is the oxygen saturation of venous blood leaving the measurement volume.

In the foregoing equation, steady blood volume measurement conditions are assumed. Therefore, blood inflow, $F_{in}$, is assumed to equal blood outflow, $F_{out}$.

Dividing equation (1) by the tissue volume sampled by the spectrometer $V_{tissue}$ results in:

$$\frac{d[HbO_2]}{dt} = -\frac{OC}{4V_{tissue}} + \frac{F}{V_{tissue}}[HbT]_{blood}(S_{a,O_2} - S_{v,O_2}) \qquad (2)$$

Assuming that the measured tissue oxygen saturation $S_{O2}$ is the average of the oxygen saturations of arterial blood $S_{a,O2}$ and venous blood $S_{v,O2}$ and further assuming that the total blood hemoglobin concentration $[HbT]_{tissue}$ remains constant, equation (2) can be simplified as follows:

$$\frac{dSO_2}{dt} = \frac{OC}{4[HbT]_{tissue}V_{tissue}} + \frac{2F_{blood}}{V_{tissue}}\frac{[HbT]_{blood}}{[HbT]_{tissue}}(S_{a,O_2} - SO_2) \qquad (3)$$

The solution to equation (3) subject to the initial condition that $SO_2(t=0)$ is equal to the measured tissue $SO_2$ at $t=0$ ($SO_{2,init}$) can be written as:

$$SO_2(t) = S_{a,O_2} - \frac{(OC/V_{tissue})}{8(F_{blood}/V_{tissue})[HbT]_{blood}} + \qquad (4)$$

$$\left(SO_{2,init} - S_{a,O_2} + \frac{(OC/V_{tissue})}{8(F_{blood}/V_{tissue})[HbT]_{blood}}\right)$$

$$\exp\left(-\frac{2F_{blood}}{V_{tissue}}\frac{[HbT]_{blood}}{[HbT]_{tissue}}\right)$$

By fitting equation (4) to time-resolved tissue oxygenation measurements, the parameters ($OC/V_{tissue}$) and $F_{blood}/V_{tissue}$), which represent volumetric oxygen consumption and volumetric blood flow per unit tissue volume, can be estimated.

The specific derivation shown above is valid for the case in which blood inflow equals blood outflow. The derivation can, however, readily be generalized to accommodate the case in which the blood inflow into the measurement volume and the blood outflow out of the measurement volume are different, i.e., $F_{in} \neq F_{out}$.

We write a mass balance for oxygenated hemoglobin ($HbO_2$) within the measurement volume ($V_t$)[1]:

$$\frac{d[HbO_2]}{dt} = -\frac{OC}{4V_t} + \frac{F_{in}[HbT]_b S_{a,O_2}}{V_t} - \frac{F_{out}[HbT]_b S_{v,O_2}}{V_t} \qquad (5)$$

where $[HbO_2]$ is the molar concentration of oxygenated hemoglobin in tissue (in moles per liter), OC is the tissue oxygen concentration (mol $O_2 \cdot s^{-1}$), Fin and Fout are the amounts of blood flow into and out of the measurement volume (in $Ls^{-1}$), respectively, $[HbT]_b$ is the blood total hemoglobin concentration (in moles per liter) and is interchangeable with $[HbT]_{blood}$, and $S_{a,O2}$ and $S_{v,O2}$ are the arterial and venous oxygen saturation (expressed as percentages, e.g., $S_{a,O2}$=98% of the hemoglobin in arterial blood is in the form of oxygenated hemoglobin ($HbO_2$)), respectively.

Furthermore, the relationship between blood inflow and outflow in the measurement volume can be expressed as:

$$F_{out} = F_{in} - \frac{d[HbT]_t}{dt}\frac{V_t}{[HbT]_b} \qquad (6)$$

Where [HbT]t is the tissue hemoglobin concentration (in moles per liter). The near-infrared measurement of tissue hemoglobin saturation ($SO_2$) represents a weighted average of the arterial and venous saturations: $SO_2 = fS_{a,O2} + (1-f)S_{v,O2}$. As follows, the venous oxygen saturation $S_{v,O2}$ may be expressed as:

$$S_{v,O_2} = \frac{SO_2 - fS_{a,O_2}}{1-f} \qquad (7)$$

The time-derivative of the relationship $[HbO_2]=SO_2[HbT]_t$, is derived using the chain rule:

$$\frac{d[HbO_2]}{dt} = SO_2\frac{d[HbT]_t}{dt} + [HbT]_t\frac{dSO_2}{dt} \qquad (8)$$

Rewriting equation (5) gives:

$$SO_2\frac{d[HbT]_t}{dt} + [HbT]_t\frac{dSO_2}{dt} = \qquad (9)$$

$$-\frac{OC}{4V_t} + \frac{F_{in}[HbT]_b S_{a,O_2}}{V_t} - \left(\frac{F_{in}[HbT]_b}{V_t} - \frac{d[HbT]_t}{dt}\right)\frac{SO_2 - fS_{a,O_2}}{1-f}$$

Dividing by $[HbT]_t$ and grouping terms by $SO_2(t)$ gives:

$$\frac{dSO_2}{dt} = \frac{1}{[HbT]_t} \qquad (10)$$

$$\left(-\frac{OC}{4V_t} + \frac{F_{in}[HbT]_b S_{a,O_2}}{V_t} + \left(\frac{F_{in}[HbT]_b}{V_t} - \frac{d[HbT]_t}{dt}\right)\frac{fS_{a,O_2}}{1-f}\right) +$$

$$\frac{SO_2}{[HbT]_t}\left(-\left(\frac{F_{in}[HbT]_b}{V_t} - \frac{d[HbT]_t}{dt}\right)\frac{1}{1-f} - \frac{d[HbT]_t}{dt}\right)$$

A measurement of $d[HbT]_t/dt$, shown in equation (8), may be expressed as an ordinary differential equation with time-variable coefficients in the following form:

$$\frac{dSO_2(t)}{dt} = a + bSO_2(t), \qquad (11)$$

$$SO_2(t=0) = SO_{2,init}$$

Where:

$$a = \frac{1}{[HbT]_t} \qquad (12)$$

$$\left(-\frac{OC}{4V_t} + \frac{F_{in}[HbT]_b S_{a,O_2}}{V_t} + \left(\frac{F_{in}[HbT]_b}{V_t} - \frac{d[HbT]_t}{dt}\right)\frac{fS_{a,O_2}}{1-f}\right)$$

$$b = -\frac{1}{[HbT]_t}\left(\left(\frac{F_{in}[HbT]_b}{V_t} - \frac{d[HbT]_t}{dt}\right)\frac{1}{1-f} + \frac{d[HbT]_t}{dt}\right)$$

The solution to Equation (11) subject to the initial condition $SO_2(t=0=SO_{2,unit}$ (the measured value of $SO_2$) is:

$$SO_2(t) = -\frac{a}{b} + \left(SO_{2,init} + \frac{a}{b}\right)\exp(bt) \qquad (13)$$

with a and b given above in equation (12). A data analysis based on the model provided Equations (11) and (12) is described in the Example 2 below.

Three dimensional images of blood flow (BF) and oxygen consumption (OC) can be obtained by applying the fitting procedure explained above to every voxel in a time-resolved tomographic reconstruction of the hemoglobin species concentration for a tissue of interest. In principle, blood flow and oxygen concentration can be imaged directly by incorporating either of the metabolic models described above into a image reconstruction algorithm.

Figure 1B:
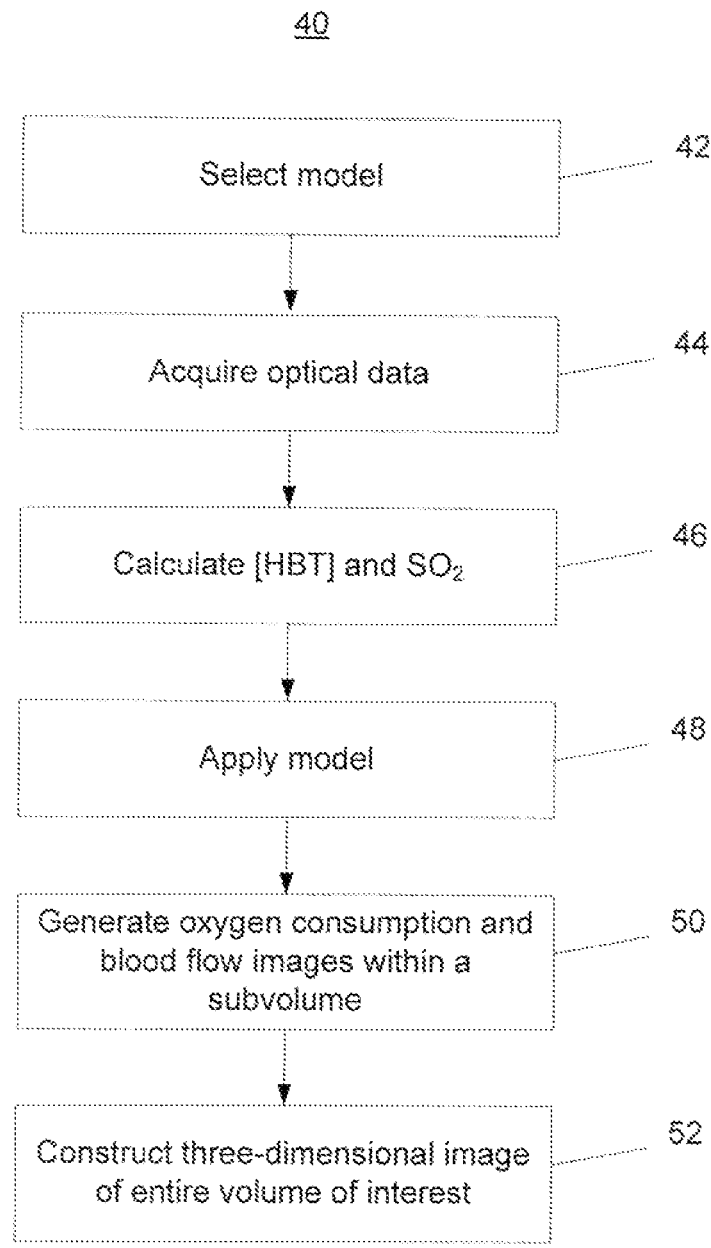
FIG. 1B shows a flowchart of a process for imaging blood flow and oxygen consumption in a volume of tissue.

FIG. 1B describes a process 40 for constructing images of blood flow and oxygen consumption within elements of a tissue of interest. The process 40 may be run on the computer 20 shown in FIG. 1 or one or more other computers. The process 40 selects (42) a metabolic model stored in memory. For example, the process 40 may select (42) the metabolic model described in Equation (4) and that relies on the assumption that the blood flow into the tissue is approximately equal to the blood flow out of the tissue. Alternatively, the process 40 may select (42) the metabolic model described in Equations (11) and (12), which does not assume that the blood inflow and outflow are the same. The selection of the model may depend on a variety of factors including the type of tissue being evaluated, patient vital signs, tissue properties, and other factors that would affect the validity of various model constraints.

The process 40 acquires (44) optical measurements obtained using the system 10 shown in FIG. 1A. To obtain the measurements, multiple delivery fibers 24 deliver electromagnetic energy to multiple collection sites within the tissue of interest. Multiple collection fibers 28 collect the energy after it has passed through the tissue and deliver it to the RF spectrometer 26, which in turn, provides measurement data to the computer 20 for processing.

Using known methods, from the measurement data, the process 40 determines (46) values for the tissue oxygen, saturation $SO_2$, and the total hemoglobin concentration in tissue $[HbT]_{tissue}$. The total hemoglobin concentration of blood $[HbT]_{blood}$ is determined by taking a blood sample or by selecting a value in the normal physiological range without measurement. The $SO_2$ and [HbT] values are determined for each of the collection sites within the tissue of interest. Each collection site represents a subvolume with the entire tissue volume. The process 40 may derive the oxygen saturations of arterial blood $S_{a,O2}$ and venous blood $S_{v,O2}$ from the tissue oxygen saturation $S_{O2}$ value according to one or more applied constraints. For example, as described above, oxygen saturations of arterial blood $S_{a,O2}$ and venous blood $S_{v,O2}$ may be derived according to the following relationship: $SO_2 = fS_{a,O2} + (1-f)S_{v,O2}$, where f is a predefined value. For example, One possible choice is f=0.5 then $SO_2$ is the average of the venous and arterial saturations. The value for f can be selected based on prior knowledge of the tissue vascular topography (from perhaps another medical imaging method) or can be selected to match values published in the scientific literature. Alternatively, $S_{a,O2}$ could be measured using a pulse oximeter.

Figure 12:
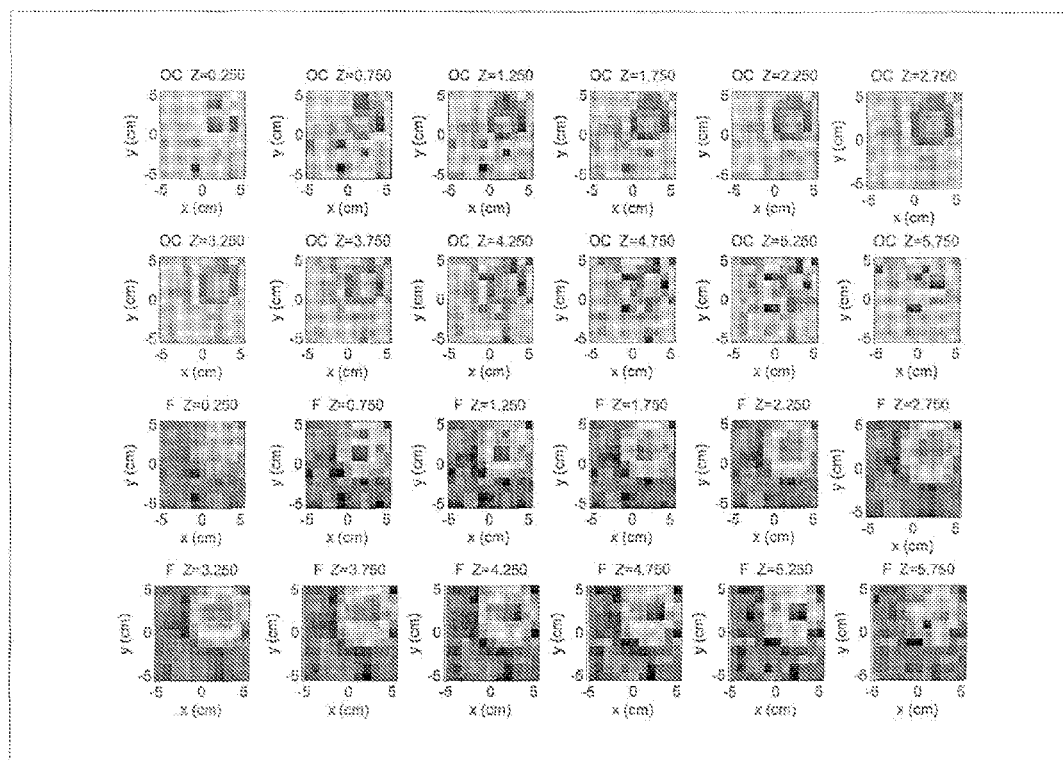
FIG. 12 shows images of blood flow and oxygen consumption for different cross sections of a simulated volume of interest.

For each subvolume, the process 40 applies (48) the model to the [HbT] and $SO_2$ values, and the values derived therefrom. The model estimates the volumetric blood flow and volumetric oxygen consumption for each subvolume. In some embodiments, a subvolume represents a cross-section of the entire volume of interest. The volumetric blood flow and volumetric oxygen consumption within each subvolume are represented as two-dimensional tomographic images that are generated (50) by the process 40. Examples of two-dimensional tomographic images are shown in FIG. 12 of Example 3.

A three-dimensional images of the entire volume of interest may be constructed (52) from the individual images of the subvolumes using tomographic reconstruction. A time-resolved three-dimensional image of blood flow and oxygen consumption may also be constructed from measurements as they acquired (44) repeatedly over an extended period of time. Example 3 (below) describes a simulation study in which tomographic images of a simulated volume of interest were constructed.

The methods described herein offer a convenient way to simultaneously measure both blood flow and oxygen consumption in breast tissue. Software for carrying out the method can be integrated into optical breast scanners. For examples, such software can be integrated into an instrument that combines the X-ray tomosynthesis machine 32 with optical imaging. Such software can also be integrated into instruments that combine optical imaging with digital radiography, and in particular, with digital tomosynthesis. The techniques described above can be used standalone, or also in conjunction with breast MRI, including HOLD tMRI (time-resolved measurement of deoxy-hemoglobin content).

Contrary to those concerns that have been raised regarding the adverse effect, on optical imaging under mammographic compression, of blood depletion, at least 50-70% of the initial blood volume remains even during a 20 lb mammographic compression. This remaining blood is sufficient for effective optical tomography. Because of the higher interstitial pressure associated with malignant lesions, breast tissue afflicted with such malignancies would be expected to retain an even greater percentage of blood volume under mammographic compression. As a result, mammographic compression would actually enhance the tumor/normal tissue contrast during optical imaging.

In addition, a hyperemic effect has been discovered, in which total hemoglobin concentration rises above its initial level upon release of compression. A characteristic of the hyperemic affect, for example its extent or duration, may be indicative of the presence of malignant tumors and/or lesions. As a result, the optical imaging method described herein can exploit the hyperemic effect to detect the existence of malignancies in the breast.

EXAMPLES

Example 1

A multi-modality system was used to perform simultaneous diffuse optical tomography with X-ray tomosynthesis for imaging angiogenesis related to large breast tumors. One notable feature of this system was that optical imaging was performed under mammographic compression. A pilot study was carried out to assess the effect of compression on optical measurements, to ascertain physiological parameters of the breast under mammographic-like compression, and to identify dynamic features that could lead to enhancement of the diagnostic ability of system.

Using an RF spectrometer 26 operated in same-side reflective configuration, concentrations of hemoglobin species at various compression plateaus were obtained from fifty-six healthy volunteers. Volumetric blood flow and volumetric oxygen consumption were also estimated for selected volunteers based on the time-course of the hemoglobin oxygen saturation.

In the breast compression spectroscopy system 10 shown schematically in FIG. 1, computer controlled translation stage 12 applied between 0 and 12 lbs of compression to the subject's breast 16 which was placed between upper and lower plastic compression plates of the compression frame 14. The lower plate, which was table mounted on a support, contained optical fibers for delivery and collection of near-infrared radiation.

The near-infrared measurements were performed with a frequency-domain tissue spectrometer (model 96208, manufactured by ISS, Inc. of Champaign, Ill.). This instrument used four parallel photomultiplier tube detectors that were time shared by eight multiplexed laser diodes. The eight diodes emitted light in the NIR band, specifically at 635, 670, 691, 752, 758, 782, 811, and 831 nm. The frequency of intensity modulation was 110 MHz, and heterodyne detection was performed with a cross-correlation frequency of 5 kHz. A complete acquisition cycle over the eight wavelengths was completed every 80 milliseconds.

The laser diodes and the photomultiplier tubes were all coupled to fiber optics. The eight individual delivery fibers 24, each having an internal diameter of 400 μm, were arranged into a fiber bundle having a rectangular cross-section of 3.5 mm×2.0 mm. There were three bundles of collection fibers 28, each of which had a 3.0 mm internal diameter. The faces of the delivery and collection fibers were flush with the lower plate and arranged along a line 1.5 cm from the edge of the plate, with the three collecting fiber bundles at distances of 1.5 cm, 2.0 cm and 2.9 cm from the center of the bundle of delivery fibers 24.

Each volunteer's breast was placed in contact with the lower plate of the compression system with her chest wall resting against the edge of the plate. The upper plate was then brought down until it just made contact with the breast. Baseline optical properties were recorded for 30-90 seconds. Then, 3 lbs of force were applied and the position held for 30 seconds, after which the force was increased to 6 lbs. Optical properties were then acquired for another 30-90 seconds. The upper plate was then moved up until all compression was released. This entire cycle was repeated a total of 3-5 times. For some subjects, a four step cycle was also used, in which the breast was compressed for ten seconds at four different compression force plateaus: 0, 3, 6 and 12 lbs.

The tissue optical absorption ($\mu_a$) and scattering ($\mu_s'$) coefficients were derived from the frequency domain measurements using a multi-distance fitting algorithm as described by Fantini, et al., "Quantitative determination of absorption spectra of chromophores in scattering media: a light emitting diode based technique," Appl. Opt. vol. 33, pages 5204-13 (1994) and by Fantini et al., "Semi-infinite geometry boundary problem for light migration in highly scattering media: a frequency-domain study in the diffusion approximation," J. Opt. Soc. Am. B, vol. 11, pages 2128-38 (1994). The dependence on the source/detector separation of the measured DC and AC components ($I_{DC}$, $I_{AC}$) as well as the phase ($\phi$) of the diffusely reflected light was predicted by diffusion theory as follows:

$$ln(r^2 I_{DC}) = r S_{DC}(\mu_a, \mu_s') + C_{DC} \quad (5)$$

$$ln(r^2 I_{AC}) = r S_{AC}(\mu_a, \mu_s') + C_{AC} \quad (6)$$

$$\phi = r S_\phi(\mu_a, \mu_s') + C_\phi, \quad (7)$$

where $S_{DC}$, $S_{AC}$, and $S_\phi$ were the slopes characterizing the relationship between $ln(r^2 I_{DC})$, $ln(r^2 I_{AC})$, and $\phi$, and the source-detector separation r, $C_{DC}$, $C_{AC}$, $C_\phi$ were constants independent of r. Again, from diffusion theory (if $r\sqrt{3\mu_n\mu_x'} \gg 1$), then:

$$\mu_a = \frac{\omega}{2c_t}\left(\frac{S_\phi}{S_{AC}} - \frac{S_{AC}}{S_\phi}\right) \quad (8)$$

$$\mu_x' = \frac{S_{AC}^2 - S_\phi^2}{3\mu_a} - \mu_a \quad (9)$$

where ω is the modulation frequency of the light sources, and $c_t$ is the speed of light in tissue. The $\mu_a(\lambda)$ calculated from equation (8) was then corrected for water absorption: $\mu_a^w(\lambda) = \mu_a(\lambda) - C_{water} \mu_{water}(\lambda)$. In doing so, a value of 0.3 was assumed for the water fraction in breast tissue ($C_{water}$).

In determining the oxy-hemoglobin concentration [HbO$_2$] and the deoxy-hemoglobin concentration [HbR], an assumption was made that $\mu_a^w(\lambda) = C_{HbO2} \mu_{a,HbO2}(\lambda) + C_{HbR} \mu_{a,HbR}(\lambda)$, or in matrix form:

$$\mu_a^w = \mu_{a,Hb} C \quad (10)$$

where $\mu_a^w = (\mu_a^w, \lambda_{min}; \ldots; \mu_a^w, \lambda_{max})$ was the vector containing the water-corrected absorption coefficient values, $C = (\mu_{a,HbO2}, \mu_{a,HbR})$ was a vector reflecting the concentration of the hemoglobin species, and $\mu_{a,Hb} = (\mu_{a, HbO2, \lambda min}, \mu_{a,HbR,\lambda min}; \ldots; \mu_{a, HbO2,\lambda max}, \mu_{a,HbR,\lambda max})$ was a matrix containing the absorption spectra of the hemoglobin species at the measurement wavelengths. Finally, inverting equation (10) resulted in:

$$C = (\mu_{a,Hb}^T * \mu_{a,Hb})^{-1} * \mu_{a,Hb}^T * \mu_a^w \quad (11)$$

Figure 2:
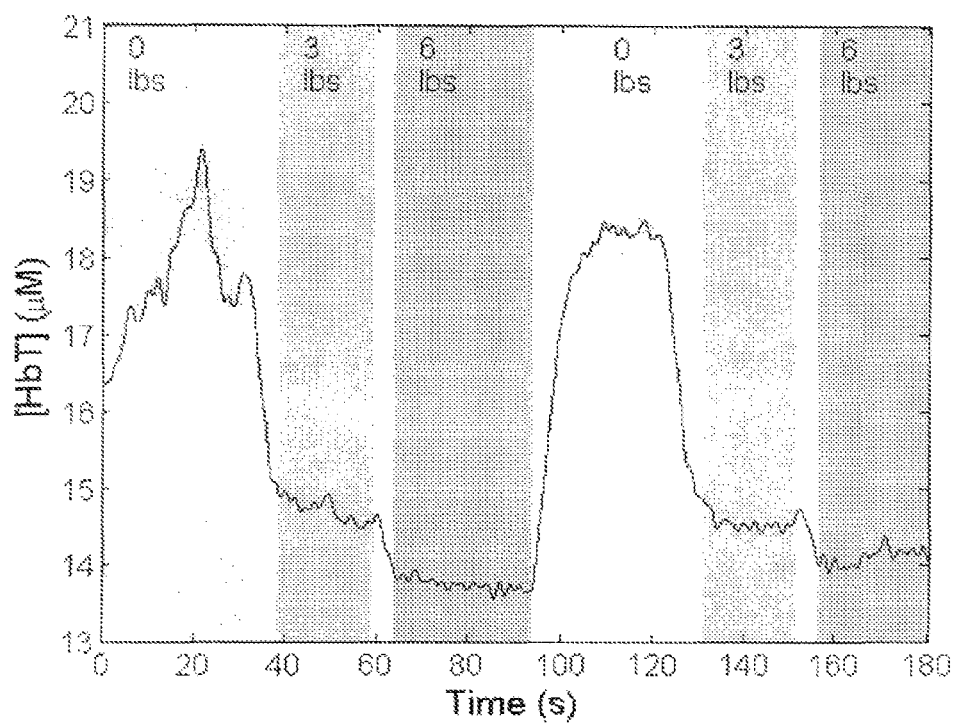
FIG. 2 shows sample total hemoglobin concentration ([HbT]) recording at different compression plateaus.

FIG. 2 shows a plot 54 of a representative recording of the total hemoglobin content acquired during two consecutive compression cycles for a thirty-year old woman having a body mass index of 25. The shading in the figure indicates the compression force plateaus used during the experiment. There was a notable drop in total hemoglobin concentration, most of which occurs in the transition between the 0 lb compression plateau and the 3 lb compression plateau. As shown in Table 1, when averaged over the entire patient set, a drop of 13.5±10% (mean±standard deviation) in total hemoglobin concentration ([HbT]) corresponded to the application of 3 lbs of compression force, with a further drop of 3.9±4% resulting from application of a 6 lb compression force. For those five subjects who agreed to undergo 12 lbs of compression, an extra 5% decrease in total hemoglobin concentration, was observed in the transition between the 6 lb and 12 lb compression plateaus.

TABLE 1

Changes in total hemoglobin concentration averaged over all measurements. (*Only 5 subjects tested at 12 lb compression plateau).

| Compression plateau (lbs) | Relative blood volume change | Standard deviation |
|---|---|---|
| 0 → 3 | −13.5% | 10% |
| 3 → 6 | −3.9% | 4% |
| 6 → 12* | ~−5% | (insufficient samples) |

Figure 3:
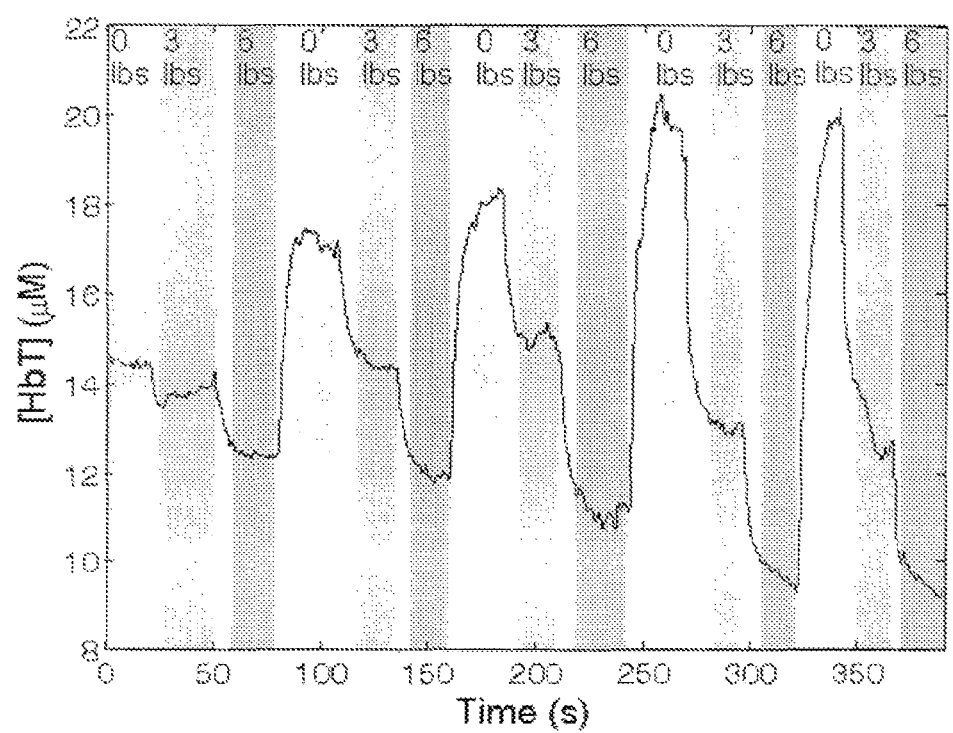
FIG. 3 shows data suggestive of reactive hyperemia during repeated compression cycles at different compression plateaus.

FIG. 3 shows a plot 56 of total hemoglobin recording illustrating another physiological effect of breast compression; hyperemia. As can be seen in the figure, upon releasing compression after the first cycle, the total hemoglobin concentration, does not simply return to the baseline level. Instead, the total hemoglobin concentration significantly exceeds the baseline level. The overshoot in total hemoglobin concentration continues to increase in later cycles, and in the end stabilizes at approximately 25% beyond the initial baseline of total hemoglobin concentration. The extent of the hyperemic effect varied widely between subjects, the case shown here being one of the more extreme ones.

Figure 4:
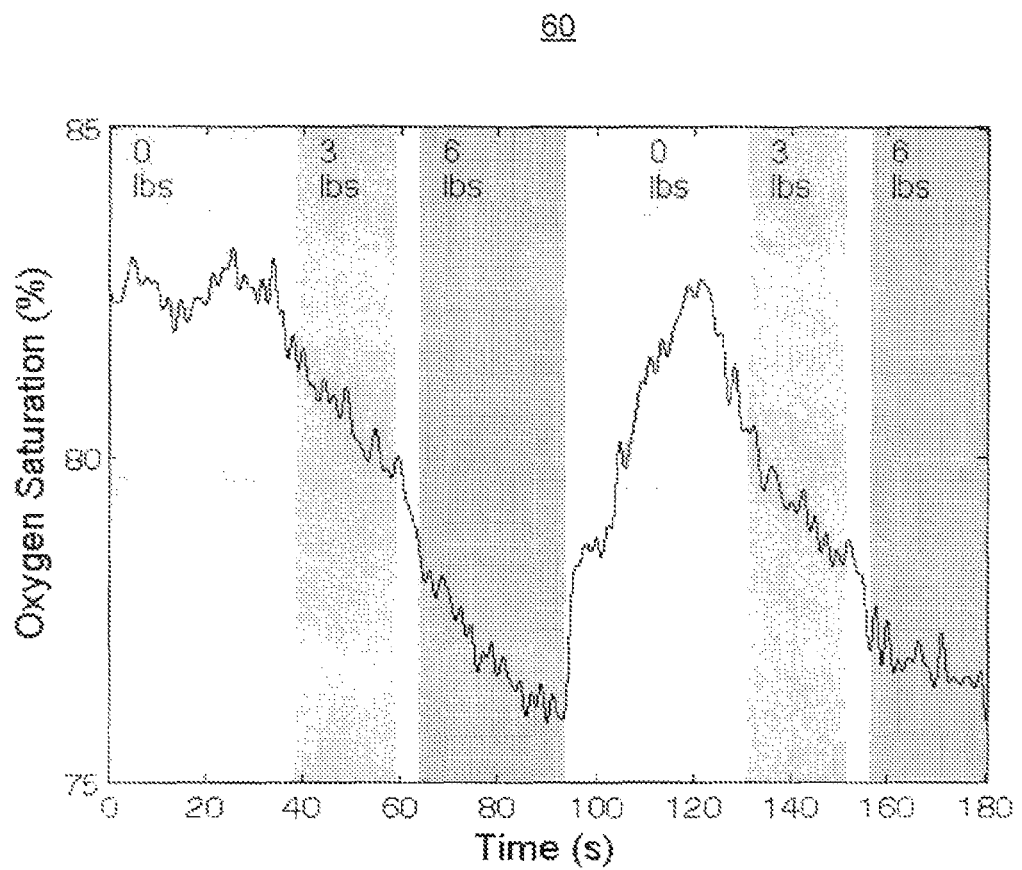
FIG. 4 shows data representative of hemoglobin oxygen saturation ($SO_2$)

FIG. 4 shows a plot 60 of a time-resolved measurement of the hemoglobin oxygen saturation for the same subject as FIG. 2. While the tissue oxygen-saturation ($SO_2$) was relatively constant when no pressure was applied, it decreased during the compression plateaus. This decrease suggested that blood flow had been at least partially occluded, thereby interfering with replenishment of oxygen consumed by the tissue. Upon compression relief, the tissue oxygen saturation returned to the pre-compression value, but did so more slowly than the recovery in total hemoglobin concentration levels.

Figure 5:
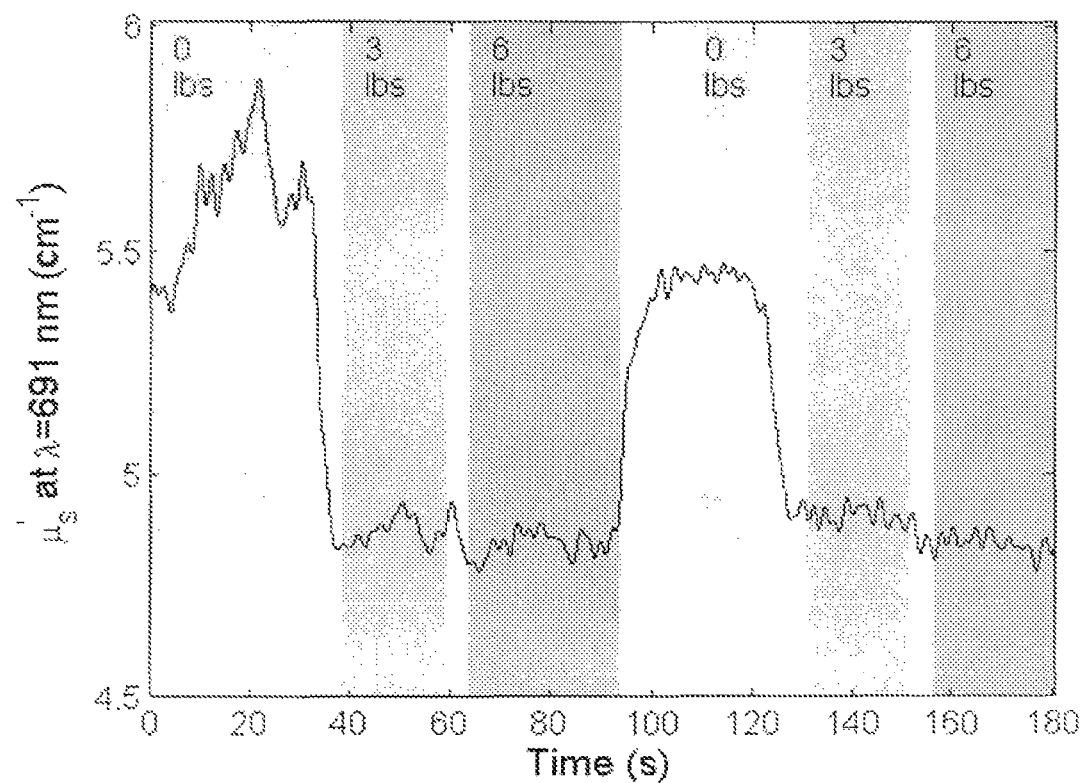
FIG. 5 shows data representative of scattering coefficient ($\mu_s'$) at $\lambda$=691 nm at different compression plateaus.

As shown in the plot 70 of FIG. 5, changes in optical scattering during breast compression generally mimicked the changes in total hemoglobin concentration. This suggested a correlation between the optical scattering and total hemoglobin concentration.

Finally, as noted above, hemoglobin oxygen saturation steadily decreased in all subjects during the compression plateaus. Consequently, the time-resolved profile of tissue oxygen-saturation from the 6 lb compression step for 10 subjects for whom the compression plateau lasted for 90 seconds was fitted to the transient state model described previously to estimate the volume-normalized blood flow and oxygen consumption, thus providing absolute measurements of breast tissue oxygen consumption and volumetric blood flow by optical methods.

Figure 6:
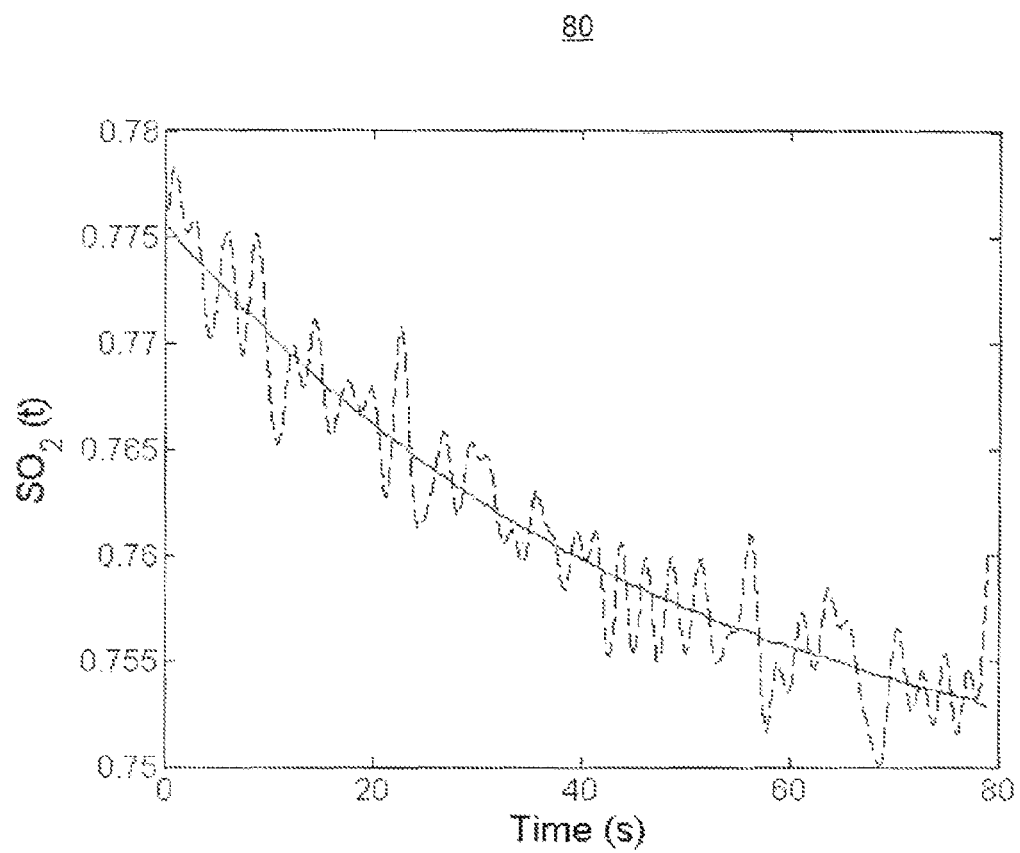
FIG. 6 shows an exemplary fit of $SO_2(t)$ measured data against a predicted curve.

FIG. 6 shows a plot 80 of an example fit to the measured oxygen-saturation profile using equation (4). The small oscillations in tissue oxygen-saturation were probably artifacts caused by the cardiac cycle. These oscillations suggested that compression resulted in reduction, and not cessation of blood flow. Table 2 summarizes the oxygen consumption and blood flow findings. Average blood flow was 1.64±0.6 mL/100 mL/min, while average oxygen consumption was 1.97±0.6 μmol/100 mL/min.

TABLE 2

Volume normalized blood flow and oxygen consumption for ten subjects during 90 second, 6 lb compression plateaus.

| Subject | Blood flow (mL/100 mL/min) | Oxygen consumption (μmol/100 mL/min) |
|---|---|---|
| 1 | 1.41 | 1.90 |
| 2 | 2.38 | 2.31 |
| 3 | 2.83 | 2.71 |
| 4 | 0.64 | 0.75 |
| 5 | 1.90 | 2.52 |
| 6 | 1.80 | 2.24 |
| 7 | 1.51 | 2.34 |
| 8 | 1.00 | 1.17 |
| 9 | 1.58 | 2.09 |
| 10 | 1.35 | 1.63 |

Figure 7:
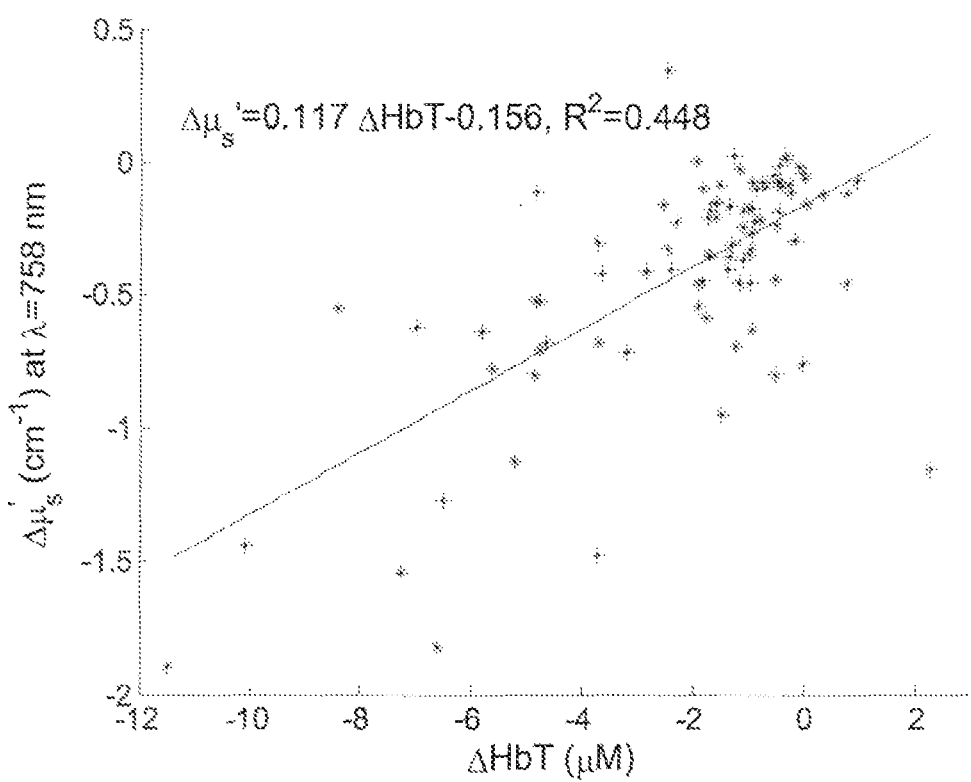
FIG. 7 shows a correlation between changes in [HbT] and a scattering coefficient ($\mu_s'$).

FIG. 7 shows a plot 90 of a Correlation between changes in [HbT] and $\mu_s'$. The solid line indicates the linear fit, while the star (*) symbols indicate individual measurements. From the optical scattering measurements, a certain degree of correlation ($R^2$=0.45) has been found between the change in $\mu_s'$ and the change in the total hemoglobin concentration. However, the data suggests a change of 0.12 cm$^{-1}$ in $\mu_s'$, for every μM of HbT, which in turn would indicate that blood is responsible for approximately half of the tissue scattering. It is believed that other tissue components that co-vary with HbT during compression must account for the additional scattering changes, such as water and lipid concentration.

Example 2

Using the breast compression spectroscopy system 10 shown schematically in FIG. 1A, concentration of hemoglobin species at various compression plateaus were obtained from twenty-eight volunteers. Volumetric blood flow and volumetric oxygen consumption were also estimated for selected volunteers based on the time-course of the hemoglobin oxygen saturation.

The computer controlled translation stage applied 6 lbs of compression to the subject's breast 16, which was placed between upper and lower plastic compression plates of the compression frame 14. The lower plate, which was table mounted on a support, contained optical fibers for delivery and collection of near-infrared radiation having the same characteristics as in Example 1.

The data analysis assumed that $S_{a,O2}$=0.98, f=0.5, and $[HbT]_b$=0.72 mM. The value of $[HbT]_b$ was selected based on the following considerations. While normal hemoglobin concentration is in the range of 120-160 g/L for females according to R. Berkow, M. H. Beers, R. M. Bogin, and A. J. Fletches, *The Merck Manual of Medical Information (Home Edition)*, chapter A.III, "Common Medical Test", pages 1375-1376. Merck Research Laboratories, Whitehouse Station, N.J. 1997, the blood in the region probed by the spectrometer 26 was dominantly contained in capillary vessels, whose hematocrit values were known to be 2-5 times lower than the systemic hematocrit (due to the Fahracus effect). Based on this knowledge, the data analysis assumed a systemic hemoglobin concentration of 140 g/L and a 3 times dilution factor in the capillaries. From the systemic hemoglobin concentration and dilution factor values, a value of 0.72 mM was determined for $[HbT]_b$. Although the choice of $[HbT]_b$ may influence the flow results, it may not affect the calculated oxygen consumption because the inflow and outflow terms appear as part of a product with $[HbT]_b$ in the mass balance Equations (1) and (2).

Figure 8A:
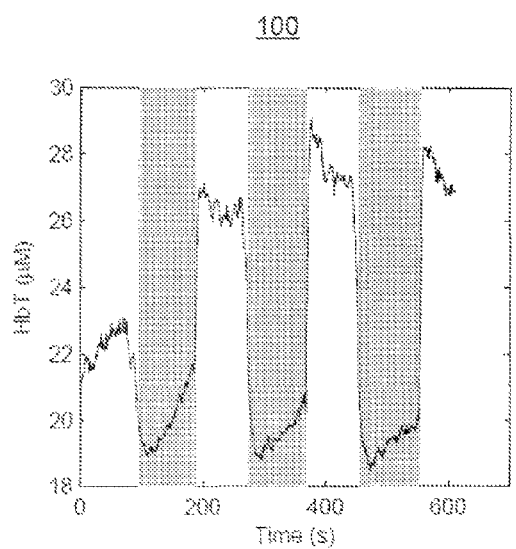
FIGS. 8A and 8B show [HbT] and $SO_2$ recordings at different compression plateaus.
Figure 8B:
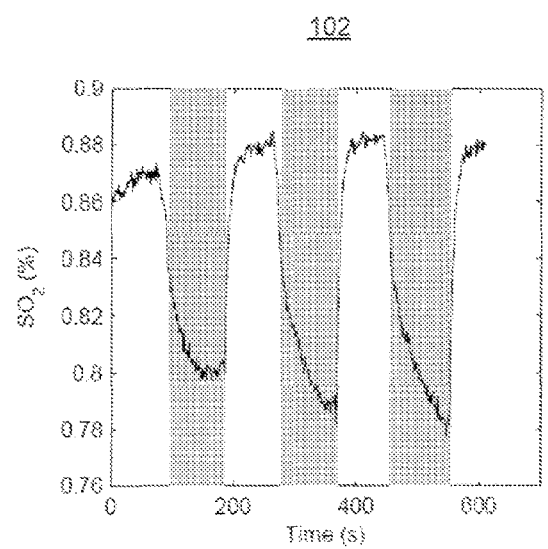

FIGS. 8A-8B show plots 100 and 120 of representative recording of the total hemoglobin content [HbT] and the hemoglobin oxygen saturation $SO_2$, respectively, that were acquired from one of the subjects during the three consecutive compression cycles. The shading in FIGS. 1A-B indicates the compression force plateaus used during the experiment.

An initial fast decrease in [HbT] is observed when compression is applied followed by a slow recovery after the compression plates stop moving, $SO_2$ also decreases as compression is applied and the change appears to correlate with the concomitant reduction in [HbT]. The initial decrease is followed by a continued slower decrease with roughly an exponential decay profile. A notable feature in the $SO_2$ traces shown in FIG. 1 is the apparent correlation between $SO_2$ and [HbT] most evident in the $SO_2$ decrease during the initial compression phase.

Figure 9A:
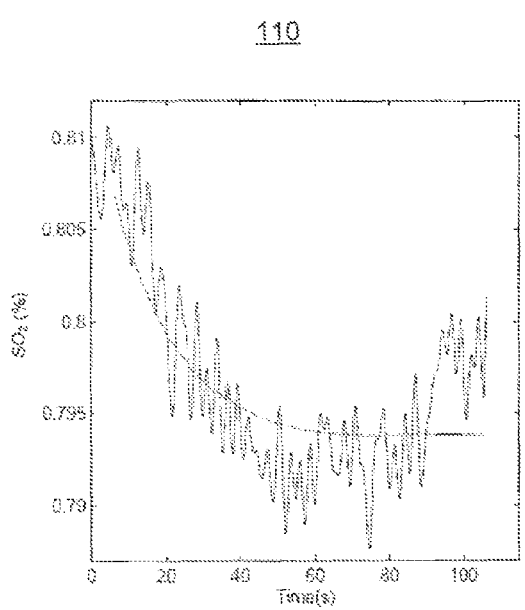
FIGS. 9A and 9B show exemplary fits of $SO_2(t)$ measured data against predicted curves without (9A) and with (9B) correction of $SO_2(t)$ based on [HbT](t).

FIG. 9A shows a plot 110 of a sample hemoglobin oxygen saturation ($SO_2$) recording acquired during steady compression together with metabolic model fit that was generated using Equations (11) and (12). As seen in FIG. 9A the metabolic model does not fit well the later portion of the $SO_2$ trace, particularly during the period of 80-100 s. A possible explanation for this deviation is that the [HbT] change affects the $SO_2$ recording in ways not accounted for in the blood flow/oxygen consumption model. For example, the initial decrease in blood volume and the small decrease in saturation observed during the initial compression, as seen in FIGS. 8A-B, may account for errors in the fit. To obtain a more accurate model fit, the sample hemoglobin oxygen saturation ($SO_2$) recording of FIG. 9A was modified using an empirical approach that calculated the ratio of the relative [HbT] drop to the relative $SO_2$ reduction during initial compression for each cycle. This ratio is referred to as a "correlation factor". The empirical approach then used the correlation factor to subtract the [HbT] driven component of the $SO_2$ recording.

Figure 9B:
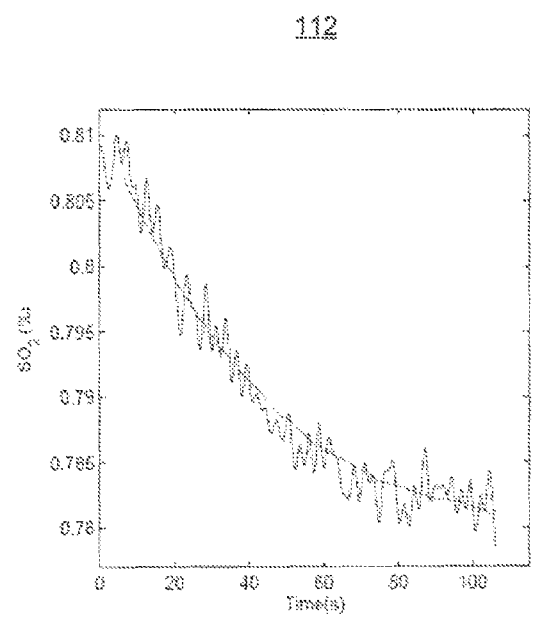

FIG. 9B shows a modified $SO_2$ curve resulting from applying the empirical approach to the hemoglobin oxygen saturation ($SO_2$) recording of FIG. 9A. FIG. 9B also shows a model fit to the modified $SO_2$ curve that was generated using Equations (11) and (12). The model fit of FIG. 9B appears to be more accurate than the model fit of FIG. 9A, particularly during the period of 80-100 s.

Table 3 displays the average volumetric blood flow and oxygen consumption estimated from the volunteer data set.

umes near the top of the volume 140 represent optical detectors, which detect the energy passing through the volume 140. The metabolic model was used to simulate the evolution of $[HbT]_{tissue}$ and $SO_2$ in the simulation volume 140. The subvolumes within the spherical inclusion 142 had larger blood flow and oxygen consumption values than the subvolumes outside of the spherical inclusion. The volume outside the spherical inclusion is referred to as the "background." From these values optical properties were predicted and diffuse optical tomography data was generated (124) using the Photon Migration Imaging (PMI) toolbox available from http://www.nmr.mgh.harvard.edu/PMI/resources/toolbox.htm, as described below.

Figure 10:
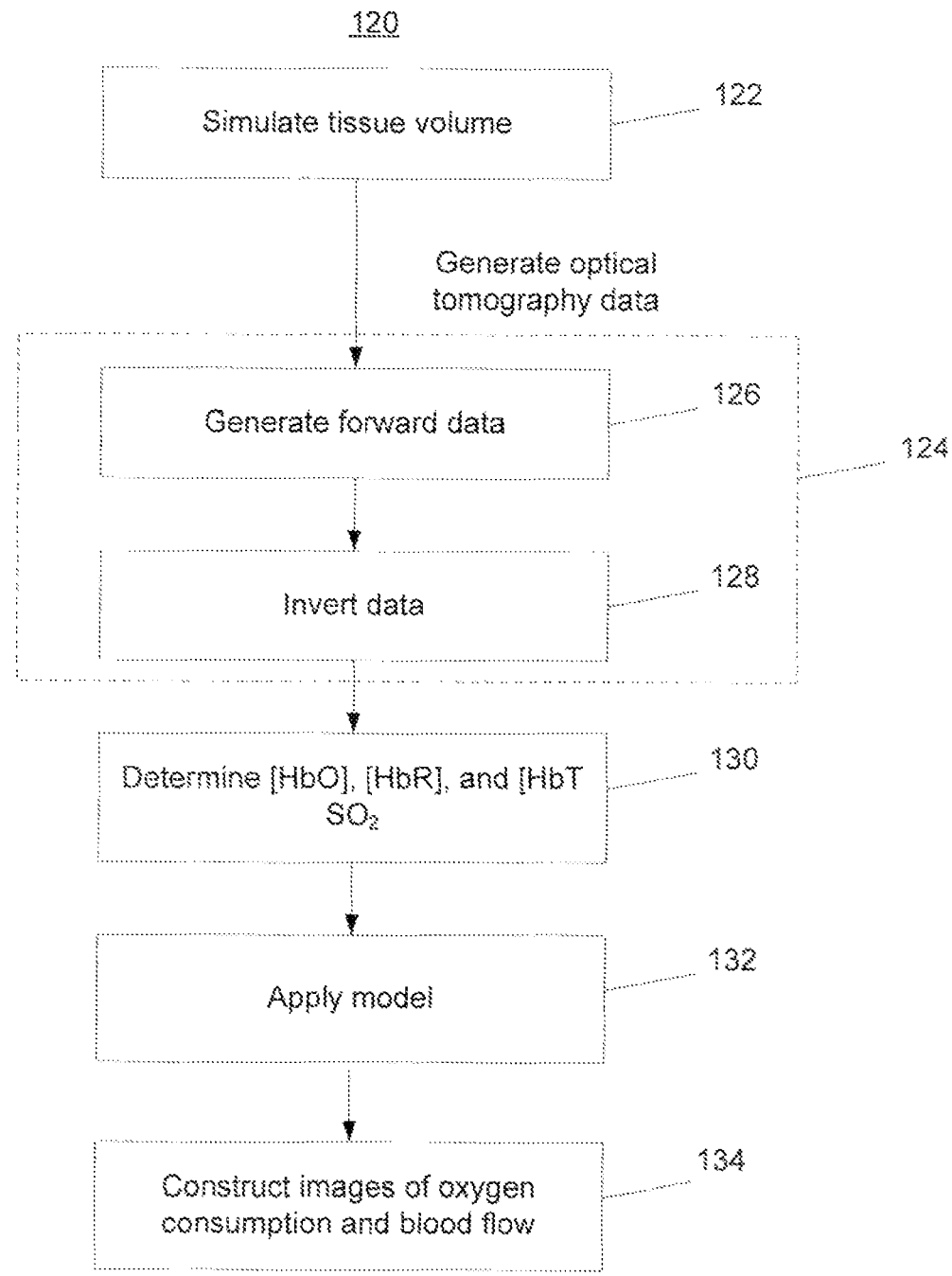
FIG. 10 shows a flowchart of a process for generating a images of blood flow and oxygen consumption in a simulated volume of interest.

Referring back to FIG. 10, forward data was generated (126) for each optical source. Forward data represent simulated optical measurements. Forward data with added noise was then inverted (128) to recover the optical properties that were initially selected based on the blood flow and oxygen consumption chosen for the "background" and "inclusion."

Using the forward data with added noise, and without knowledge of the structural heterogeneity of the simulation volume, optical properties were reconstructed again using the PMI Toolbox at multiple time instants and from these properties, $[HbT]_{tissue}$ and $SO_2$ values were calculated for

TABLE 3

Volume normalized blood flow and oxygen consumption during 1 lb. compression plateaus.

|  | Cycle 1 | Cycle 2 | Cycle 3 |
| --- | --- | --- | --- |
| Oxygen Consumption | 1.53 μmol/100 mL/min | 1.63 μmol/100 mL/min | 1.41 μmol/100 mL/min |
| Blood Flow | 1.47 ml/100 mL/min | 1.59 ml/100 mL/min | 1.34 ml/100 mL/min |

The average values of both oxygen consumption (1.52 μmol/100 mL/min) and blood flow (1.47 mL/100 mL/min) are very close to the averages obtained in Example 1, which are shown above to be 1.97 μmol/100 mL/min and 1.64 mL/100 mL/min, respectively. However, unlike in Example 1, in which only those data sets having sufficient SNR and exhibiting a largely constant $[HbT]_{tissue}$ were used for estimating oxygen consumption and blood flow, the oxygen consumption and blood flow values shown in Table 3 were obtained using metabolic model of Equations (11) and (12) applied to all volunteer data sets having sufficient SNR, i.e., certain data sets were handpicked to be discarded due to apparent high measurement noise. Typically, acceptable $SO_2$ noise is less than approximately 0.2-0.5% and also the shape of the recording should be relatively be free of artifacts. Assuming acceptable SNR, the model used in this example, by contrast to the model used in Example 1, can be applied to all the data, not just those that exhibit relatively constant $[HbT]_{tissue}$.

Example 3

The following study was performed to provide a three dimensional image of blood flow and oxygen consumption of a stimulated volume of interest using the metabolic model described above in Equations (11) and (12). The flowchart of FIG. 10 describes the process 120 of the simulation study. A tissue volume was modeled (122) as a cube shaped volume 140, which is shown in FIG. 11.

Figure 11:
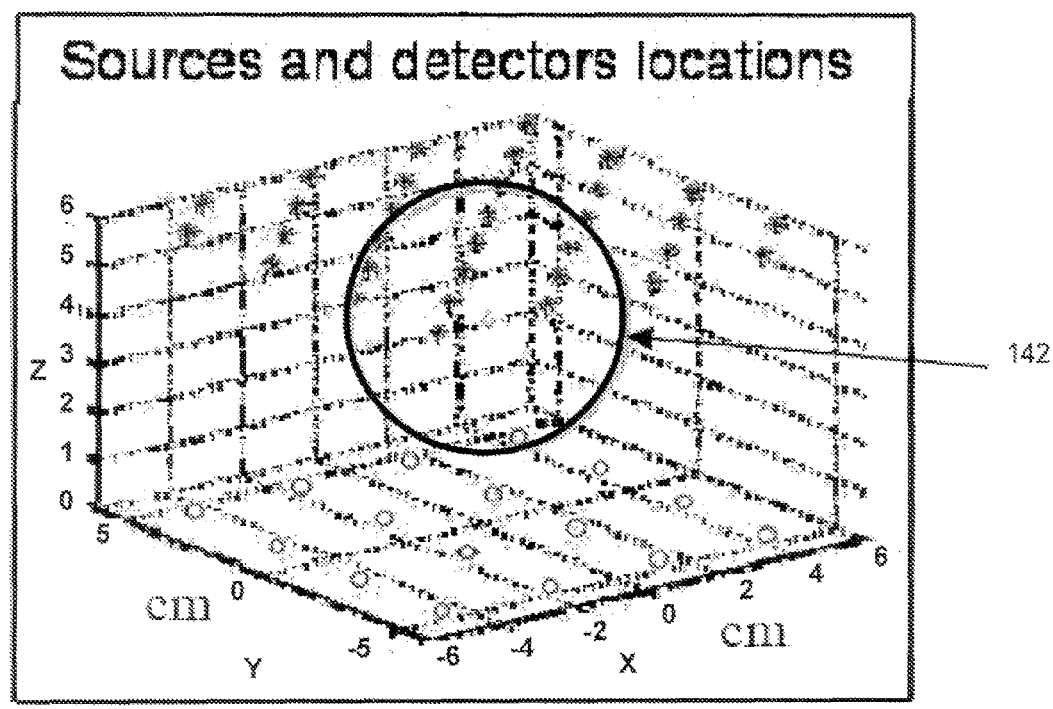
FIG. 11 shows a simulated volume of interest.

As shown in FIG. 11, the volume 140 includes a tumor modeled as a spherical inclusion 142. The volume 140 was divided into subvolumes. The circular markings within subvolumes near the bottom of the volume 140 represent optical sources, from which energy is delivered to the volume 140, and the star-shaped markings within subvolevery subvolume in the simulation volume. In particular, values for the tissue oxygen saturation $SO_2$, the total hemoglobin concentration of blood $[HbT]_{tissue}$, deoxy-hemoglobin concentration of blood $[HbO]_{tissue}$, and oxygenated hemoglobin concentration $[HbT]_{tissue}$ were determined (130) for each of the subvolumes. Oxygen saturations of arterial blood $S_{a,O2}$ and venous blood $S_{v,O2}$ were derived from the tissue oxygen saturation $SO_2$ value using following relationship: $SO_2 = f\, S_{a,O2} + (1-f) S_{v,O2}$, where f was selected to be 0.5, meaning that the measured $SO_2$ is assumed to be the average of the arterial and venous hemoglobin saturations. The total hemoglobin concentration in tissue $[HbT]_{tissue}$ was reconstructed.

For each subvolume, the process 120 applies (132) the model to produce estimates of the volumetric blood flow and volumetric oxygen consumption from their time courses. In some embodiments, a subvolume represents a cross-section of the entire volume of interest. Two-dimensional tomographic images of the volumetric blood flow and volumetric oxygen consumption within each subvolume were constructed.

FIG. 12 shows cross-sectional images 150 of oxygen consumption and blood flow for 12 subvolumes for a 5% change in $[HbT]_{tissue}$ and a 60 dB SNR.

Table 4 presents the volume averages of blood flow and oxygen consumption for the background and inclusion subvolumes obtained for various levels of applied measurement noise and $[HbT]_{tissue}$ variation. The blood flow and oxygen consumption parameters reconstructed for the background and tumor inclusion have the units (mL/100 mL/min) and (μmol/100 mL/min), respectively. The line marked with (*) indicates the data corresponding to the plots in FIG. 12.

TABLE 2

Summary of BF (in mL/100 mL/min) and OC (in μmol/100 mL/min) parameters reconstructed for the background and the tumor inclusion for various levels of simulated measurement noise [HbT]$_{tissue}$ variation.

| HbT change | SNR | Tumor OC avg. | Tumor OC std. dev. | Background OC avg. | Background OC std. dev. | Tumor F avg. | Tumor F std. dev. | Background F avg. | Background F std. dev. |
|---|---|---|---|---|---|---|---|---|---|
| Actual Value | | 3.36 | 0.00 | 2.24 | 5.00 | 3.44 | 0.00 | 1.38 | 0.00 |
| 10% | no noise | 3.31 | 0.17 | 2.24 | 0.05 | 2.91 | 0.49 | 1.37 | 0.04 |
| 10% | 60 dB | 3.29 | 0.21 | 2.22 | 0.17 | 2.90 | 0.51 | 1.36 | 0.10 |
| 10% | 50 dB | 3.26 | 0.43 | 2.18 | 0.51 | 2.87 | 0.62 | 1.34 | 0.30 |
| 10% | 40 dB | 3.34 | 1.90 | 2.09 | 1.72 | 2.95 | 1.78 | 1.28 | 1.02 |
| 5% | no noise | 3.44 | 0.20 | 2.23 | 0.08 | 3.03 | 0.39 | 1.37 | 0.05 |
| 5% (*) | 60 dB | 3.44 | 0.24 | 2.28 | 0.30 | 3.02 | 0.41 | 1.40 | 0.19 |
| 5% | 50 dB | 3.43 | 0.43 | 2.13 | 0.78 | 3.01 | 0.48 | 1.31 | 0.48 |
| 5% | 40 dB | 3.41 | 1.22 | 2.44 | 3.43 | 3.02 | 1.18 | 1.49 | 2.09 |
| 0 | no noise | 3.64 | 0.35 | 2.22 | 0.16 | 3.21 | 0.24 | 1.37 | 0.10 |
| 0 | 60 dB | 3.62 | 0.41 | 2.15 | 0.51 | 3.19 | 0.24 | 1.33 | 0.32 |
| 0 | 50 dB | 3.52 | 0.51 | 2.31 | 1.61 | 3.10 | 0.37 | 1.44 | 1.00 |
| 0 | 40 dB | 3.21 | 1.39 | 2.28 | 2.97 | 2.84 | 1.24 | 1.41 | 1.85 |

An excellent accuracy is observed even in the presence of [HbT]$_{tissue}$ variation and simulated measurement noise.

It is apparent from the foregoing experiments that breast compression leads to changes in total hemoglobin concentration, hemoglobin oxygen saturation, and tissue scattering. The steady decrease in hemoglobin saturation observed during compression plateaus enabled quantitative estimates of the tissue metabolic state. These estimates have the potential to aid cancer detection. While changes in breast optical properties during compression were significant, they are unlikely to impede tomographic optical imaging once taken into account. Furthermore, the compression-induced dynamic features of the changes in optical physiological properties of breast tissue, as well as changes in the tissue oxygen consumption, may depend in part on the presence of cancerous tissue. Accordingly, these quantities may provide useful diagnostic information.

Other Embodiments

The method has been described thus far in the context of breast cancer. However, increased oxygen consumption is a characteristic of cancer cells anywhere they are located. Hence, the method described herein is not restricted to compression of breast tissue, but can be applied to any tissue.

In addition, the method can also be carried out by comparing data from any two compression states. There is no requirement that one compression state be characterized by a 0 lb compression plateau. The compression pressure, which depends on breast size, is typically strong enough to impede or partially impede blood flow and may range between 0.5 and 4.5 lbs/square inch.

In addition, there is no requirement that measurements be made in any particular order. One can obtain measurements from different compression states in any order that is convenient.

Having described the invention, and a preferred embodiment thereof, what we claim as new, and secured by Letters Patent is:

1. A method for producing a report indicative of a status of a tissue, the method comprising:
   a) varying a compression state of a tissue;
   b) acquiring measurement data from the tissue using a medical imaging system while the compression state of the tissue is varied;
   c) generating an estimate of at least one of oxygen saturation and hemoglobin concentration in the tissue from the acquired measurement data;
   d) computing at least one of volumetric blood flow and volumetric oxygen consumption in the tissue using a metabolic model and the generated estimate of at least one of oxygen saturation and hemoglobin concentration in the tissue; and
   e) generating a report of the computed at least one of volumetric blood flow and volumetric oxygen consumption:
   wherein the metabolic model employs a relationship given by:

$$SO_2(t) = S_{a,O_2} - \frac{(OC/V_{tissue})}{8(F_{blood}/V_{tissue})[HbT]_{blood}} + \left(SO_{2,init} - S_{a,O_2} + \frac{(OC/V_{tissue})}{8(F_{blood}/V_{tissue})[HbT]_{blood}}\right) \exp\left(\frac{2F_{blood}[HbT]_{blood}}{V_{tissue}[HbT]_{tissue}} \cdot t\right)$$

where $SO_2(t)$ denotes an oxygen saturation with respect to time t, $SO_{2,init}$ denotes an initial estimated oxygen saturation, $F_{blood}/V_{tissue}$ denotes volumetric blood flow per unit tissue volume, $OC/V_{tissue}$ denotes volumetric oxygen consumption per unit tissue volume, $S_{a,O_2}$ denotes an oxygen saturation of blood entering the tissue, and $[HbT]_{blood}$ and $[HbT]_{tissue}$ denote hemoglobin concentration in blood and the tissue, respectively.

2. The method as recited in claim 1 wherein the report includes an image reconstructed from the measurement data.

3. The method as recited in claim 1 wherein step c) includes generating a time-resolved estimate of at least one of oxygen saturation and hemoglobin concentration in the tissue.

4. The method as recited in claim 1 wherein:
   the measurement data acquired in step b) is optical image data acquired from a plurality of selected portions of the tissue using an optical spectroscopy system;
   the estimate of at least one of oxygen saturation and hemoglobin concentration generated in step c) includes a time-resolved estimate of oxygen saturation and time-resolved estimate of hemoglobin concentration associated with each of the selected portions of the tissue; and step d) includes using the metabolic model to estimate a volumetric blood flow and volumetric oxygen consumption for the selected portions of the tissue from corresponding ones of the generated time-resolved estimates of oxygen saturation and hemoglobin concentration.

5. The method as recited in claim 4 wherein the optical spectroscopy system is at least one of a radio frequency (RF) spectroscopy system and a hybrid continuous-wave/RF spectroscopy system.

6. The method as recited in claim 4 wherein step b) includes illuminating the selected portions of the tissue with near-infrared energy and acquiring the optical image data by detecting near-infrared radiation scattered from the selected portions of the tissue using a plurality of collection fibers of the optical spectroscopy system.

7. The method as recited in claim 1 wherein step a) includes varying the compression between a plurality of predetermined compression states in order to induce changes in blood flow in the tissue and dynamically alter oxygen saturation and total hemoglobin concentration in the tissue.

8. The method as recited in claim 4 wherein the report includes an image reconstructed from the time-resolved estimate of at least one of oxygen saturation and hemoglobin concentration that is indicative of differences in metabolic activity between healthy and cancerous portions of the tissue.

9. The method as recited in claim 4 wherein step d) includes reconstructing an image using the metabolic model by fitting the relationship to the time-resolved estimates of oxygen saturation for at least one of each pixel of the image and each voxel of the image.

10. The method as recited in claim 1, wherein the medical imaging system is at least one of a mammography system, an x-ray tomosynthesis system, and a magnetic resonance imaging (MRI) system having an integrated optical spectroscopy apparatus.

11. A method for producing a report indicative of a status of a tissue, the method comprising:
 a) varying a compression state of a tissue;
 b) acquiring measurement data from the tissue using a medical imaging system while the compression state of the tissue is varied;
 c) generating an estimate of at least one of oxygen saturation and hemoglobin concentration in the tissue from the acquired measurement data;
 d) computing at least one of volumetric blood flow and volumetric oxygen consumption in the tissue using a metabolic model and the generated estimate of at least one of oxygen saturation and hemoglobin concentration in the tissue; and
 e) generating a report of the computed at least one of volumetric blood flow and volumetric oxygen consumption;
 wherein the metabolic model employs a relationship given by:

$$\frac{dSO_2(t)}{dt} = a + bSO_2(t), SO_2(t=0) = SO_{2,init}$$

$$a = \frac{1}{[HbT]_t}\left(-\frac{1}{4}\frac{OC}{V_t} + \frac{F_{in}[HbT]_b S_{a,O_2}}{V_t} + \left(\frac{F_{in}[HbT]_b}{V_t} - \frac{d[HbT]_t}{dt}\right)\frac{fS_{a,O_2}}{1-f}\right)$$

-continued
$$b = -\frac{1}{[HbT]_t}\left(\left(\frac{F_{in}}{V_t}[HbT]_b - \frac{d[HbT]_t}{dt}\right)\frac{1}{1-f} + \frac{d[HbT]_t}{dt}\right)$$

where $SO_2$ (t) denotes an oxygen saturation with respect to time t, $SO_{2,unit}$ denotes an initial estimated oxygen saturation, $$\frac{OC}{V_t}$$

denotes volumetric oxygen consumption per unit tissue volume, $$\frac{F_{in}}{V_t}$$

denotes volumetric blood flow per unit tissue volume into the tissue, $[HbT]_b$ and $[HbT]_t$ denote hemoglobin concentration in blood and the tissue, respectively, and f is a weighting factor.

12. The method as recited in claim 11 wherein the weighting factor f is selected based on prior knowledge of vascular topology in the tissue.

13. A device for producing a report indicative of a status of a tissue, the device comprising:
 a force applicator configured to produce a series of selected compression states in a tissue;
 an imaging apparatus configured to acquire measurement data from the tissue; and
 a processor configured to compute at least one of volumetric blood flow and volumetric oxygen consumption in the tissue during the series of selected compression states and to generate report on a pathological status of the tissue using a metabolic model;
 wherein the model employs a relationship given by:

$$SO_2(t) = S_{a,O_2} - \frac{(OC/V_{tissue})}{8(F_{blood}/V_{tissue})[HbT]_{blood}} + \left(SO_{2,init} - S_{a,O_2} + \frac{(OC/V_{tissue})}{8(F_{blood}/V_{tissue})[HbT]_{blood}}\right)\exp\left(\frac{2F_{blood}[HbT]_{blood}}{V_{tissue}[HbT]_{tissue}} \cdot t\right)$$

where $SO_2$ (t) denotes an oxygen saturation with respect to time t, $SO_{2,unit}$ denotes an initial estimated oxygen saturation, $F_{blood}/V_{tissue}$ denotes volumetric blood flow per unit tissue volume, $OC/V_{tissue}$ denotes volumetric oxygen consumption per unit tissue volume, $S_{a,O_2}$ denotes an oxygen saturation of blood entering the tissue, and $[HbT]_{blood}$ and $[HbT]_{tissue}$ denote hemoglobin concentration in blood and the tissue, respectively.

14. The device as recited in claim 13 wherein the processor is further configured to generate a time-resolved estimate of at least one of oxygen saturation and hemoglobin concentration from acquired measurement data to generate the report on a pathological status of the tissue.

15. The method as recited in claim 14 wherein step d) includes reconstructing an image using the metabolic model by fitting the relationship to a time-resolved estimates of hemoglobin concentration for at least one of each pixel of the image and each voxel of the image.

16. The device as recited in claim 14 wherein the processor is further configured to reconstruct an image by fitting the relationship to the time-resolved estimates of oxygen saturation for at least one of each pixel of the image and each voxel of the image.

17. The device as recited in claim 14 wherein the processor is further configured to reconstruct an image indicative of at least one of volumetric blood flow and volumetric oxygen consumption in the tissue using a model that relates changes in oxygen saturation levels and hemoglobin concentration to volumetric blood flow and volumetric oxygen consumption and provide the image as the report.

18. The device as recited in claim 13 further comprising a motion controller coupled to the force applicator and processor and configured to control the force applicator to automatically produce the series of selected compression states in response to instructions from the processor.

19. The device as recited in claim 18 wherein the series of selected compression states are selected to induce changes in blood flow in the tissue and alter oxygen saturation and hemoglobin concentrations in the tissue.

20. The device as recited in claim 13 wherein the imaging apparatus includes a source of electromagnetic radiation configured to illuminate the tissue and a detector configured to detect electromagnetic radiation scattered from within the tissue.

21. The device as recited in claim 20 wherein the device is configured to be incorporated into at least one of a mammography system, an x-ray tomosynthesis system, and a magnetic resonance imaging (MRI) system.

22. The device as recited in claim 13 wherein the imaging apparatus is at least one of a RF spectroscopy system and a continuous-wave/RF spectroscopy system.

23. A device for producing a report indicative of a status of a tissue, the device comprising:
a force applicator configured to produce a series of selected compression states in a tissue;
an imaging apparatus configured to acquire measurement data from the tissue; and
a processor configured to compute at least one of volumetric blood flow and volumetric oxygen consumption in the tissue during the series of selected compression states and to generate report on a pathological status of the tissue using a metabolic model;
wherein the model employs a relationship given by:

$$\frac{dSO_2(t)}{dt} = a + bSO_2(t), SO_2(t=0) = SO_{2,init}$$

$$a = \frac{1}{[HbT]_t}\left(-\frac{1}{4}\frac{OC}{V_t} + \frac{F_{in}[HbT]_b S_{a,O_2}}{V_t} + \left(\frac{F_{in}[HbT]_b}{V_t} - \frac{d[HbT]_t}{dt}\right)\frac{fS_{a,O_2}}{1-f}\right)$$

$$b = -\frac{1}{[HbT]_t}\left(\left(\frac{F_{in}}{V_t}[HbT]_b - \frac{d[HbT]_t}{dt}\right)\frac{1}{1-f} + \frac{d[HbT]_t}{dt}\right)$$

where $SO_2$ (t) denotes an oxygen saturation with respect to time t, $SO_{2,init}$ denotes an initial estimated oxygen saturation, $$\frac{OC}{V_t}$$

denotes volumetric oxygen consumption per unit tissue volume, $$\frac{F_{in}}{V_t}$$

denotes volumetric blood flow per unit tissue volume into the tissue, $[HbT]_b$ and $[HbT]_t$ denote hemoglobin concentration in blood and the tissue, respectively, and f is a weighting factor.

24. The device as recited in claim 23 wherein the weighting factor f is selected based on prior knowledge of vascular topology in the tissue.

25. The device as recited in claim 23 wherein the processor is configured to reconstruct an image using the model by fitting the relationship to a time-resolved estimates of hemoglobin concentration for at least one of each pixel of the image and each voxel of the image.

* * * * *

UNITED STATES PATENT AND TRADEMARK OFFICE
CERTIFICATE OF CORRECTION

PATENT NO.        : 10,010,277 B2
APPLICATION NO.   : 11/766444
DATED             : July 3, 2018
INVENTOR(S)       : Carp et al.

It is certified that error appears in the above-identified patent and that said Letters Patent is hereby corrected as shown below:

Column 1, Line 23, "treatment" should be --treatments--.

Column 1, Line 49, "practice" should be --practices--.

Column 2, Line 47, "predefining" should be --predefined--.

Column 3, Line 34, "for the oxygen" should be --for oxygen--.

Column 5, Line 57, "concentration" should be --consumption--.

Column 8, Line 8, "images" should be --image--.

Column 8, Line 21, "examples" should be --example--.

Column 8, Line 27, "HOLD tMRI" should be --BOLD fMRI--.

Column 12, Line 11, "concentration" should be --concentrations--.

Column 12, Line 29, "Fletches" should be --Fletcher--.

Column 12, Line 30, "Test" should be --Tests--.

Column 12, Lines 35-36, "Fahracus" should be --Fahraeus--.

Column 13, Line 57, "stimulated" should be --simulated--.

Column 14, Line 39, "[HbT]" should be --[HbO]--.

Signed and Sealed this
Twenty-first Day of August, 2018

Andrei Iancu
*Director of the United States Patent and Trademark Office*